(12) United States Patent
Burke

(10) Patent No.: US 9,482,464 B1
(45) Date of Patent: Nov. 1, 2016

(54) CONTROLLING TEMPERATURE OF A TEST CHAMBER WHICH IS EQUIPPED WITH A REFRIGERANT COOLING SUBSYSTEM AND A LIQUID NITROGEN COOLING SUBSYSTEM

(71) Applicant: EMC Corporation, Hopkinton, MA (US)

(72) Inventor: Kevin Burke, Innishannon (IE)

(73) Assignee: EMC IP Holding Company, LLC, Hopkinton, MA (US)

( * ) Notice: Subject to any disclaimer, the term of this patent is extended or adjusted under 35 U.S.C. 154(b) by 243 days.

(21) Appl. No.: 14/143,790

(22) Filed: Dec. 30, 2013

Related U.S. Application Data

(60) Provisional application No. 61/892,893, filed on Oct. 18, 2013.

(51) Int. Cl.
*F25D 17/06* (2006.01)
*F25D 29/00* (2006.01)

(52) U.S. Cl.
CPC .................................... *F25D 29/00* (2013.01)

(58) Field of Classification Search
CPC ....... G01R 31/02; G01R 31/26; F25D 29/00; H01H 31/02
See application file for complete search history.

(56) References Cited

U.S. PATENT DOCUMENTS

| | | | |
|---|---|---|---|
| 3,710,251 A * | 1/1973 | Hagge | G01R 31/2891 324/750.08 |
| 4,918,928 A | 4/1990 | Morioka et al. | |
| 5,317,883 A * | 6/1994 | Newman | F25D 17/06 62/419 |
| 5,915,343 A * | 6/1999 | Zenobi | G01M 15/02 123/41.01 |
| 6,185,952 B1 | 2/2001 | McCollin | |
| 6,257,319 B1 | 7/2001 | Kainuma et al. | |
| 6,301,907 B1 | 10/2001 | McCollin et al. | |
| 6,710,613 B2 | 3/2004 | Sauerland | |
| 6,861,861 B2 | 3/2005 | Song et al. | |
| 6,932,635 B2 | 8/2005 | Ishikawa et al. | |
| 7,008,804 B2 | 3/2006 | Song et al. | |
| 7,049,841 B2 | 5/2006 | Yamashita | |
| 2002/0092354 A1* | 7/2002 | Peterson | G01M 7/02 73/663 |
| 2002/0109518 A1* | 8/2002 | Saito | G01R 1/0458 324/750.09 |
| 2010/0107436 A1* | 5/2010 | Velardi | F26B 5/06 34/284 |

* cited by examiner

*Primary Examiner* — Len Tran
*Assistant Examiner* — Ana Vazquez
(74) *Attorney, Agent, or Firm* — BainwoodHuang

(57) ABSTRACT

An environmental control apparatus includes a test chamber, a refrigerant cooling subsystem coupled to the test chamber, a liquid nitrogen cooling subsystem coupled to the test chamber, and control circuitry. The control circuitry is coupled to the refrigerant cooling subsystem and the liquid nitrogen cooling subsystem. The control circuitry is constructed and arranged to coordinate operation of the refrigerant cooling subsystem and the liquid nitrogen cooling subsystem to control internal temperature of the test chamber. Selective operation of the liquid nitrogen cooling subsystem and the refrigerant cooling subsystem can provide significant cost savings by alleviating the need to provide liquid nitrogen cooling in all cooling situations. Moreover, co-location of the liquid nitrogen cooling subsystem and the refrigerant cooling subsystem can provide an efficient and effective form factor for the environmental control apparatus.

13 Claims, 5 Drawing Sheets

US 9,482,464 B1

CONTROLLING TEMPERATURE OF A TEST CHAMBER WHICH IS EQUIPPED WITH A REFRIGERANT COOLING SUBSYSTEM AND A LIQUID NITROGEN COOLING SUBSYSTEM

CROSS REFERENCE TO RELATED APPLICATIONS

This Patent Application is a related to U.S. Patent Application No. 61/892,893 filed on Oct. 18, 2013 and entitled, "CONTROLLING TEMPERATURE OF A TEST CHAMBER WHICH IS EQUIPPED WITH A REFRIGERANT COOLING SUBSYSTEM AND A LIQUID NITROGEN COOLING SUBSYSTEM", the contents and teachings of which are hereby incorporated by reference in their entirety.

BACKGROUND

A conventional Environmental Stress Screening (ESS) chamber includes an insulated chamber, a fan unit, a cooling unit which uses liquid nitrogen, and an ESS controller. A computer equipment manufacturer may have multiple ESS chambers sitting side-by-side. Accordingly, the computer equipment manufacturer is able to screen computer equipment in high volume.

During operation of such an ESS chamber, computer equipment to be tested is placed in the insulated chamber, powered on, and configured to perform computerized operations. The ESS controller then runs the fan and cooling units. In response, the fan unit blows air through the cooling unit thus cooling the insulated chamber while the computer equipment performs the computerized operations.

SUMMARY

Unfortunately, there are deficiencies to the above-described conventional ESS chamber which has a liquid nitrogen cooling unit as its sole source of cooling. For example, although the liquid nitrogen cooling unit is sufficient to provide temperature ramping and temperature soaking conditions, there is a high cost involved in operating the liquid nitrogen cooling unit to simply maintain a constant temperature (i.e., during temperature soaking).

Nevertheless, if one considered replacing the liquid nitrogen cooling unit with a refrigerant cooling unit (e.g., a cooling unit that uses Freon or a Freon substitute rather than liquid nitrogen), the refrigerant cooling unit would need to be much larger to match the temperature ramp performance of the liquid nitrogen cooling unit. In particular, the refrigerant cooling unit would require larger compressors and take up significantly more floor space (e.g., perhaps twice the space consumed by the liquid nitrogen cooled ESS chamber) to provide equivalent ramp capacity.

In contrast to the above-described conventional ESS chamber which uses a liquid nitrogen cooling unit as a sole source of cooling, an environmental control system is equipped with a test chamber and a hybrid cooling subsystem to effectuate reliable and robust test chamber cooling. The hybrid cooling subsystem includes (i) a liquid nitrogen cooling subsystem and (ii) a refrigerant cooling subsystem. Such a system has the ability to provide effective high demand cooling of the test chamber by concurrently operating the liquid nitrogen cooling subsystem and the refrigerant cooling subsystem (e.g., during a temperature ramp phase in which the temperature of the test chamber is lowered very quickly). Such a system also has the ability to provide efficient low demand cooling of the test chamber by deactivating the liquid nitrogen cooling subsystem and operating just the refrigerant cooling subsystem (e.g., during a temperature soak phase in which the test chamber is maintained at a constant temperature). Such selective operation can provide significant cost savings by alleviating the need to provide liquid nitrogen cooling in all cooling situations.

One embodiment is directed to an environmental control apparatus which includes a test chamber, a refrigerant cooling subsystem coupled to the test chamber, a liquid nitrogen cooling subsystem coupled to the test chamber, and control circuitry. The control circuitry is coupled to the refrigerant cooling subsystem and the liquid nitrogen cooling subsystem. The control circuitry is constructed and arranged to coordinate operation of the refrigerant cooling subsystem and the liquid nitrogen cooling subsystem to control internal temperature of the test chamber.

In some arrangements, the control circuitry, when coordinating operation of the refrigerant cooling subsystem and the liquid nitrogen cooling subsystem, is constructed and arranged to individually operate each of the refrigerant cooling subsystem and the liquid nitrogen cooling subsystem. Accordingly, one cooling subsystem can be deactivated while the other cooling system remains activated.

In some arrangements, the control circuitry, when individually operating each of the refrigerant cooling subsystem and the liquid nitrogen cooling subsystem, is constructed and arranged to concurrently activate the refrigerant cooling subsystem and the liquid nitrogen cooling subsystem to expose electronic equipment residing in the test chamber to a temperature stress phase. During such a phase, an internal environment of the test chamber is quickly ramped from an initial temperature to a target temperature which is lower than the initial temperature to stress the electronic equipment while the electronic equipment is operating.

In some arrangements, the control circuitry, when individually operating each of the refrigerant cooling subsystem and the liquid nitrogen cooling subsystem, is constructed and arranged to activate the refrigerant cooling subsystem and concurrently deactivate the liquid nitrogen cooling subsystem to expose electronic equipment residing in the test chamber to a constant temperature phase. During such a phase, an internal environment of the test chamber is maintained at a constant temperature after the internal environment is ramped from an initial temperature to the constant temperature while the electronic equipment is operating.

In some arrangements, the control circuitry, when individually operating each of the refrigerant cooling subsystem and the liquid nitrogen cooling subsystem, is constructed and arranged to:

(A) during a non-cooling phase, deactivate the refrigerant cooling subsystem and the liquid nitrogen cooling subsystem to enable a temperature of the test chamber to reach a first temperature value, (B) during a high demand cooling phase following the non-cooling phase, concurrently operate the refrigerant cooling subsystem and the liquid nitrogen cooling subsystem to decrease the temperature of the test chamber from the first temperature value to a second temperature value that is lower than the first temperature value, and (C) during a low demand cooling phase following the high demand cooling phase, deactivate the liquid nitrogen cooling subsystem and operate the refrigerant cooling subsystem to maintain the temperature of the test chamber at the second temperature value.

In some arrangements, the refrigerant cooling subsystem includes a set of refrigerant cooling coils to provide cooling from the refrigerant cooling subsystem, and the liquid nitrogen cooling subsystem includes a set of liquid nitrogen injection nozzles to provide cooling from the liquid nitrogen cooling subsystem. In these arrangements, the set of refrigerant cooling coils and the set of liquid nitrogen injection nozzles have separate pathways to prevent mixing of refrigerant and liquid nitrogen.

In some arrangements, the environmental control apparatus further includes an air circulation subsystem to generate an air stream in the test chamber. The set of refrigerant cooling coils and the set of liquid nitrogen injection nozzles are co-located relative to the air circulation subsystem to enable shared access to the air stream.

In some arrangements, the environmental control apparatus further includes a heating subsystem coupled to the control circuitry, a portion of the heating subsystem being co-located with the set of refrigerant cooling coils and the set of liquid nitrogen injection nozzles to share access to the air stream. In these arrangements, the control circuitry is further constructed and arranged to coordinate operation of the heating subsystem with operation of the refrigerant cooling subsystem and the liquid nitrogen cooling subsystem.

In some arrangements, the set of refrigerant cooling coils and the set of liquid nitrogen injection nozzles are co-located adjacent a top region of the test chamber. Such a configuration provides an efficient and effective the form factor for the environmental control apparatus.

In some arrangements, the test chamber is constructed and arranged to house, as the electronic equipment, a set of computerized components while the computerized components electronically operate and endure stress testing to identify early life failures. Other example electronic equipment includes flash memory and magnetic storage devices, storage processor devices, analogy modules, among other electronic components and hardware.

In some arrangements, the environmental control apparatus further includes a vibration assembly coupled to the test chamber. The vibration assembly is constructed and arranged to impart physical motion to electronic equipment residing in the test chamber while the electronic equipment operates during activation and deactivation of each of the refrigerant cooling subsystem and the liquid nitrogen cooling subsystem.

In some arrangements, the control circuitry includes a common control interface to receive user input from a user, and provide user output to the user. The user input includes commands to operates the refrigerant cooling subsystem and the liquid nitrogen cooling subsystem. Additionally, the user output provides operating status from the refrigerant cooling subsystem and the liquid nitrogen cooling subsystem.

In some arrangements, the control circuitry includes a timer to control duration of the non-cooling phase, the high demand cooling phase, and the low demand cooling phase.

In some arrangements, the control circuitry includes a proportional-integral-derivative (PID) controller to provide temperature control precision throughout the different phases.

Another embodiment is directed to a method of controlling temperature of a test chamber which is equipped with a refrigerant cooling subsystem and a liquid nitrogen cooling subsystem. The method includes deactivating, during a non-cooling time period, the refrigerant cooling subsystem and the liquid nitrogen cooling subsystem to enable the temperature of the test chamber to reach a first temperature value. The method further includes concurrently operating, during a high demand cooling time period following the non-cooling time period, the refrigerant cooling subsystem and the liquid nitrogen cooling subsystem to decrease the temperature of the test chamber from the first temperature value to a second temperature value that is lower than the first temperature value. The method further includes, during a low demand cooling time period following the high demand cooling time period, deactivating the liquid nitrogen cooling subsystem and operating the refrigerant cooling subsystem to maintain the temperature of the test chamber at the second temperature value.

Another embodiment is directed to a computer program product having a non-transitory computer readable medium which stores a set of instructions to control temperature of a test chamber which is provisioned with a refrigerant cooling subsystem and a liquid nitrogen cooling subsystem. The set of instructions, when carried out by computerized circuitry, cause the computerized circuitry to perform a method of:

(A) during a non-cooling time period, deactivating the refrigerant cooling subsystem and the liquid nitrogen cooling subsystem to enable the temperature of the test chamber to reach a first temperature value;

(B) during a high demand cooling time period following the non-cooling time period, concurrently operating the refrigerant cooling subsystem and the liquid nitrogen cooling subsystem to decrease the temperature of the test chamber from the first temperature value to a second temperature value that is lower than the first temperature value; and (C) during a low demand cooling time period following the high demand cooling time period, deactivating the liquid nitrogen cooling subsystem and operating the refrigerant cooling subsystem to maintain the temperature of the test chamber at the second temperature value.

Other embodiments are directed to processes, other electronic systems and apparatus, processing circuits, computer program products, and so on. Some embodiments are directed to various methods, electronic components and circuitry which are involved in controlling temperature of a test chamber which is equipped with a refrigerant cooling subsystem and a liquid nitrogen cooling subsystem.

BRIEF DESCRIPTION OF THE DRAWINGS

The foregoing and other objects, features and advantages will be apparent from the following description of particular embodiments of the present disclosure, as illustrated in the accompanying drawings in which like reference characters refer to the same parts throughout the different views. The drawings are not necessarily to scale, emphasis instead being placed upon illustrating the principles of various embodiments of the present disclosure.

DETAILED DESCRIPTION

An environmental control system is equipped with a test chamber and a hybrid cooling subsystem to effectuate reliable and robust test chamber cooling. The hybrid cooling subsystem includes (i) a liquid nitrogen cooling subsystem and (ii) a refrigerant cooling subsystem. Such a system has the ability to provide effective high demand cooling of the test chamber by concurrently operating the liquid nitrogen cooling subsystem and the refrigerant cooling subsystem (e.g., during a temperature ramp phase in which the temperature of the test chamber is lowered very quickly). Such a system also has the ability to provide efficient low demand cooling of the test chamber by deactivating the liquid nitrogen cooling subsystem and operating just the refrigerant cooling subsystem (e.g., during a temperature soak phase in which the test chamber is maintained at constant temperature). Such selective operation can provide significant savings by alleviating the need to provide costly liquid nitrogen cooling for all cooling conditions.

Figure 1:
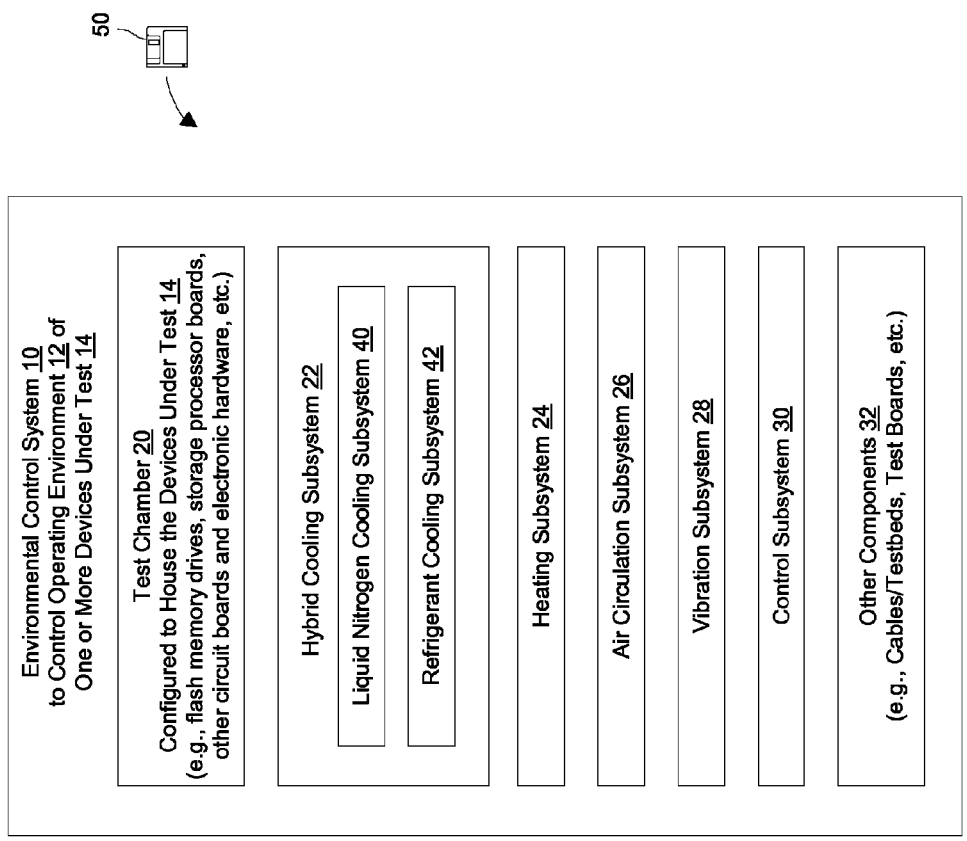
FIG. 1 is a block diagram of an environmental control system which is equipped with a hybrid cooling system.

FIG. 1 shows a block diagram of an environmental control system 10 which is capable of controlling an operating environment 12 of one or more devices under test 14. The environmental control system 10 includes a test chamber 20, a hybrid cooling subsystem 22, a heating subsystem 24, an air circulation subsystem 26, a vibration subsystem 28, a control subsystem 30, and other components 32. The hybrid cooling subsystem 22 includes a liquid nitrogen cooling subsystem 40 and a refrigerant cooling subsystem 42.

The test chamber 20 is constructed and arranged to house one or more devices under test 14 within the operating environment 12. Examples of suitable devices include flash memory and magnetic storage devices, storage processor devices, analog circuitry, combinations thereof, etc. among other electronic components and hardware. Such electronic devices typically generate heat during operation, and require some form of cooling.

The liquid nitrogen cooling subsystem 40 of the hybrid cooling subsystem 22 is constructed and arranged to operate as a high capacity cooling source (e.g., for high demand cooling during cooling ramps). The liquid nitrogen cooling subsystem 40 includes a liquid nitrogen tank, pressure relief valves, control valves, injection nozzles, etc. to provide liquid nitrogen cooling in response to control signals from the control subsystem 30.

The refrigerant cooling subsystem 42 of the hybrid cooling subsystem 22 is constructed and arranged to operate as a steady state cooling source (e.g., for low demand cooling during soak tests in which the temperature of the test chamber 20 is maintained at a constant temperature) as well as contribute towards high capacity cooling. The refrigerant cooling subsystem 40 includes a set of coils and a compressor which operate to provide refrigerant cooling in response to control signals from the control subsystem 30. The coils of the refrigerant cooling subsystem 42 and the nozzles of the liquid nitrogen cooling subsystem 40 may be substantially co-located (e.g., in close adjacency to share access to an airstream provided by the air circulation subsystem 26).

The heating subsystem 24 is constructed and arranged to operate as a heating source (e.g., to ramp up the temperature of the test chamber 20 quickly, to maintain the temperature of the test chamber 20 at a high temperature, etc.). Along these lines, the heating subsystem 24 is responsive to control signals from the control subsystem 30.

The air circulation subsystem 26 is constructed and arranged to circulate air within the test chamber 20. The air circulation subsystem 26 includes a set of blowers (or fan units), louvers, etc. which are responsive to control signals from the control subsystem 30 to provide robust and reliable air circulation among the test chamber 20, the hybrid cooling subsystem 22, and the heating subsystem 24.

The vibration subsystem 28 is constructed and arranged to provide vibration to the devices under test 14. Such vibration may simulate particular physical movements during transportation/shipping (e.g., shock or drop testing), as well as during operation (e.g., vibration testing). The vibration subsystem 28 is responsive to control signals from the control subsystem 30.

The control subsystem 30 is constructed and arranged to control the operation of the various other subsystems during testing of the devices 14. Such tests may involve operating the devices 14 at extreme temperature ranges, cycling the devices 14 through quick temperature changes, shaking the devices 14, combinations thereof, and so on. To this end, the control subsystem 30 may include processing circuitry, memory storing environmental profiles/test programs, specialized sensors to measure temperature, airflow, vibration, etc. Accordingly, the environmental control system 10 is well-suited for testing products prior to shipment, testing new designs and connections for potential failures, age testing, ambient condition testing, etc.

The other components 32 support and embellish the operation of the environmental control system 10. For example, the other components 32 may include a variety of cables, testbeds, cardcages, connectors, etc. for versatility and testing of a wide range of products. The other components 32 may further include a user interface (e.g., a computerized terminal/console to receive user input and provide user output, etc.), circuitry to electronically exercise the devices under test 14 (e.g., circuitry to provide TO operations, network traffic, raw signals, etc.), and so on.

It should be understood that at least some of the controller subsystem 30 includes processing circuitry which is constructed and arranged to operate in accordance with various software constructs stored in computerized memory. Such circuitry may be implemented in a variety of ways including via one or more processors (or cores) running specialized software, application specific ICs (ASICs), field programmable gate arrays (FPGAs) and associated programs, discrete components, analog circuits, other hardware circuitry, combinations thereof, and so on. In the context of one or more processors executing software, a computer program product 50 is capable of delivering all or portions of the software to the environmental control system 10. The computer program product 50 has a non-transitory (or non-volatile) computer readable medium which stores a set of instructions which controls one or more operations of the environmental control system 10. Examples of suitable computer readable storage media include tangible articles of manufacture and apparatus which store instructions in a non-volatile manner such as CD-ROM, flash memory, disk memory, tape memory, and the like. Further details will now be provided with reference to FIG. 2.

Figure 2:
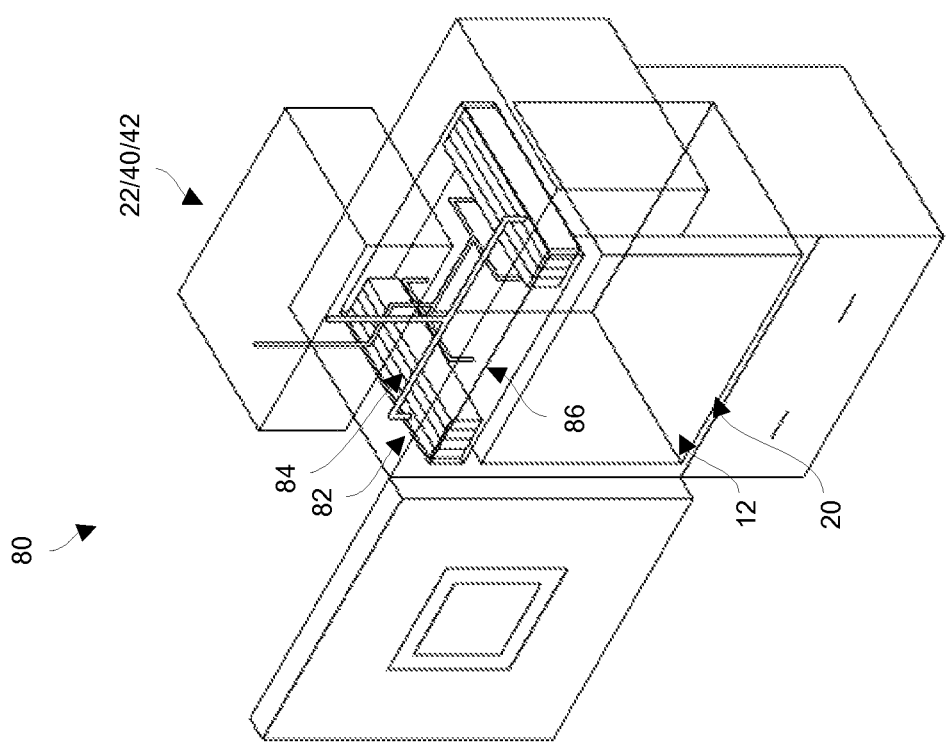
FIG. 2 is a perspective view of a particular embodiment of the environmental control system.

FIG. 2 is a perspective view of an environmental control apparatus 80, i.e., an embodiment having particular features of the environmental control system 10 of FIG. 1. It should be understood that environmental control apparatus 80 can include all of the earlier-mentioned components, but that some have been omitted from view in FIG. 2 to better illustrate particular details of the environmental control apparatus 80.

As shown in FIG. 2, the liquid nitrogen cooling subsystem 40 and the refrigerant cooling subsystem 42 of the hybrid cooling subsystem 20 are positioned above or adjacent the tops of the walls of the test chamber 20. Such an elevated location of the hybrid cooling subsystem 20 minimizes the ground-level foot print. Additionally, such a location for the hybrid cooling subsystem 20 enables convenient coupling of the liquid nitrogen cooling subsystem 40 and the refrigerant cooling subsystem 42 to other spaces (e.g., ceiling ventilation, air ducts, shared plenums, etc.).

The refrigerant cooling subsystem 42 includes sets of coils 82 which flank heating elements 84 of the heating subsystem 24. Additionally, the heating elements 84 are situated on both sides of a set of liquid nitrogen injection nozzles 86 of the liquid nitrogen cooling subsystem 40.

By way of example, there are four nozzles 86 that are configured to distribute liquid nitrogen in an effective spray pattern. The co-location of the refrigerant coils 82, the heating elements 84 and the liquid nitrogen injection nozzles 86 enables effective positioning at the top of the test chamber 20, and for all of these components to share a common airstream from the air circulation subsystem 26 (also see FIG. 1). For example, such an arrangement puts both the refrigerant coils 82 and the liquid nitrogen injection nozzles 86 near the air circulation subsystem 26 for airstream access when both are operating, or just one when only one is operating.

Figure 3:
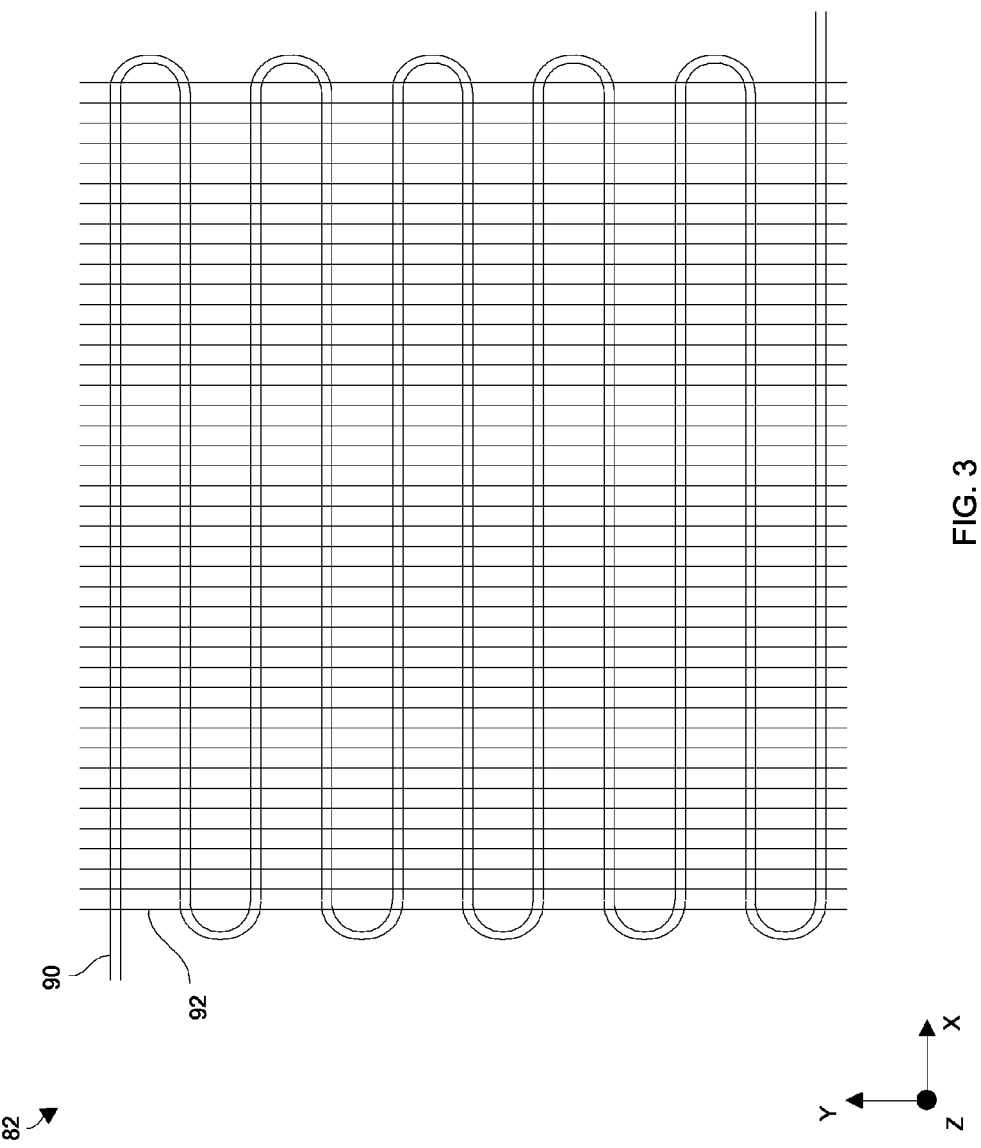
FIG. 3 is a diagram of a set of coils which are suitable for use by the environmental control system.

FIG. 3 shows a suitable coil configuration for a coil portion 82 for the refrigerant cooling subsystem 42. As shown in FIG. 3, the coil portion 82 includes piping 90 to carry either liquid nitrogen or refrigerant, and baffling 92 coupled to the piping 90. The coil portion 82 extends in X-Y plane, and enables air from the air circulation subsystem 26 to pass effectively and efficiently in the Z-direction.

In some arrangements, a heat dissipating portion of the heating subsystem 24 is interleaved with the nozzles 86 of the liquid nitrogen cooling subsystem 40 and the coil portion 82 of the refrigerant cooling subsystem 42 (also see FIG. 2). Such an arrangement enables all cooling/heating subsystems to access the same airstream of the air circulation subsystem 26. Other nozzle/coil configurations and other nozzle/coil locations are suitable for use as well. Further details will now be provided with reference to FIG. 4.

Figure 4:
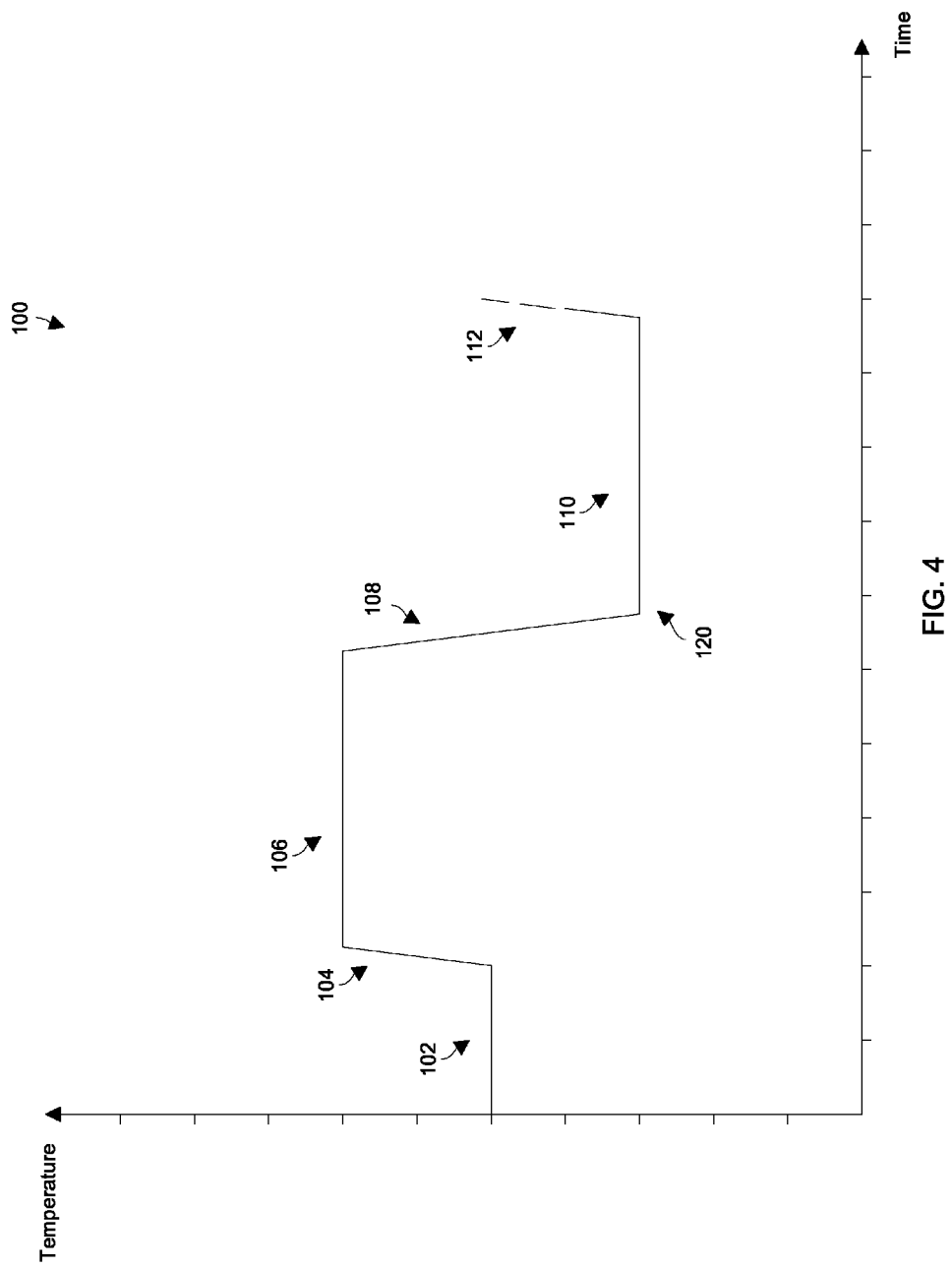
FIG. 4 is an example chart of various temperature conditions which can be provided by the environmental control system.

FIG. 4 shows an example plot 100 of time and temperature that can be provided by the environmental control system 10 during testing of the devices under test 14. It should be understood that other temperature control/behaviors can be provided by the environmental control system 10 as well.

During such operation, the control subsystem 30 (FIG. 1) operates the various components of the environmental control system 10 to stress screen the devices under test 14. During such testing, the devices under test 14 are exercised electronically (e.g., while the devices 14 perform IO operations) and may generate significant heat. Even so, the environmental control system 10 is capable of running the devices under test 14 through various test phases under different environmental conditions by operating the various subsystems separately or in combination for periods of time.

By way of example only and as illustrated in FIG. 4, the control subsystem 30 allows the devices under test 14 to run during a first phase 102 at an initial temperature such as room temperature or 25 degrees Celsius. During this first phase 102, the control subsystem 30 uses the hybrid cooling subsystem 22 to maintain the temperature relatively constant (e.g., at 25 degrees Celsius) and the vibration subsystem 28 (FIG. 1) to simulate normal operating conditions, e.g., for approximately an hour.

Next, the control subsystem 30 activates the heating subsystem 24 (FIG. 1) during a second phase 104 to sharply increase the operating temperature (i.e., a temperature ramp) until the temperature in the test chamber 20 reaches a predefined maximum test temperature (e.g., 45 degrees Celsius, 60 degrees Celsius, etc.). Since the second phase 104 is intended to be a heat ramp, the hybrid cooling subsystem 22 is deactivated during the second phase 104. Once the predefined maximum test temperature is reached, the control subsystem 30 uses the hybrid cooling subsystem 22 to maintain the temperature relatively constant for a set period of time such as approximately four hours, i.e., another phase 106.

Next, the control subsystem 30 activates both portions of the hybrid cooling subsystem 22 (FIGS. 1 and 2) during yet another phase 108 (i.e., another temperature ramp) to sharply decrease the operating temperature until the temperature in the test chamber 20 reaches a predefined minimum test temperature (e.g., −10 degrees Celsius, 0 degrees Celsius, 5 degrees Celsius, etc.). It should be understood that, if the goal is to lower the temperature as quickly as possible, the control subsystem 30 can activate both the liquid nitrogen cooling subsystem 40 and the refrigerant cooling subsystem 42 concurrently (i.e., providing high demand cooling). As a result, the temperature of the test chamber 20 can be lowered from the predefined maximum test temperature to the predefined minimum test temperature in just a few minutes.

Once the predefined minimum test temperature is reached within the test chamber 20, the control subsystem 30 uses the hybrid cooling subsystem 22 to maintain the temperature relatively constant at the low temperature for a set period of time such as approximately four hours, i.e., a low demand cooling phase 110. For example, if the refrigerant cooling subsystem 42 has enough capacity, the control subsystem 30 can deactivate the liquid nitrogen cooling subsystem 40, but continue to utilize the refrigerant cooling subsystem 42 to maintain the test chamber 20 at the low temperature. Such operation is less costly than using a conventional ESS chamber which uses a liquid nitrogen cooling unit as a sole source of cooling.

Moreover, if the refrigerant cooling subsystem 42 is unable to maintain the test chamber 20 at the low temperature, it should be understood that the control subsystem 30 can activate the liquid nitrogen cooling subsystem 40 intermittently as necessary to maintain the low temperature. Even in this situation, the cost of running the refrigerant cooling subsystem 42 continuously, and running the liquid nitrogen cooling subsystem 40 occasionally can be less expensive that the cost of running a conventional ESS chamber which uses a liquid nitrogen cooling unit as a sole source of cooling.

At the end of the low demand cooling phase 110, the control subsystem 30 then modifies operation again to provide a different condition 112. For example, the control subsystem 30 can sharply raise the temperature to repeat the above-described testing cycle back to room temperature or back to the predefined maximum temperature. As another example, the control subsystem may repeat the temperature aspects of the testing cycle but vary one or more another parameters (e.g., voltage/current, vibration, air flow, etc.) to margin test other aspects of the devices under test 14, and so on. It should be understood that throughout such temperature stressing, the devices under test 14 are continuously operated to screen for defects, and that such phases may be repeated over the course of many hours (e.g., a 24 hours, 48 hours, etc.).

As mentioned earlier, the control subsystem 30 is capable of operating both the liquid nitrogen cooling subsystem 40 and the refrigerant cooling subsystem 42 at the same time. The use of both the liquid nitrogen cooling subsystem 40 and the refrigerant cooling subsystem 42 simultaneously provides greater capacity than what only one subsystem would otherwise provide. Also, such use of both subsystems alleviates the need to provide expansive capacity of just a single cooling subsystem (i.e., if the environmental control system included only a liquid nitrogen cooling subsystem or only a refrigerant cooling subsystem) that would greatly increase equipment costs and/or the system footprint.

Such operation may involve using a timer to maintain activation of the liquid nitrogen cooling subsystem 40 for a short period of time (e.g., a few minutes) even after the temperature of the test chamber 20 reaches the target lower temperature (e.g., −10 degrees Celsius). Alternatively, or in combination, such operation may involve using a proportional, integral, derivative (PID) control circuit. Accordingly, the environmental control system 10 is able to provide different temperature effects, greater temperature accuracy, and so on.

In some arrangements, use of a PID control circuit provides better temperature accuracy, i.e., less bouncing above and below a target temperature. Rather, highly precise temperature curves can be achieved (e.g., see arrow 120 in FIG. 4).

Also, as mentioned earlier, during a steady low temperature phase in which the devices under test 14 are maintained at a low operating temperature, the environmental control system 10 is capable of providing low demand cooling. In this situation, the control subsystem 30 mainly deactivates the liquid nitrogen cooling subsystem 40 and operates the refrigerant cooling subsystem 42. The use of only the refrigerant cooling subsystem 42 lowers the operating cost of the environmental control system 10 since the refrigerant cooling subsystem 42 is less expensive to run than the liquid nitrogen cooling subsystem 40. Additionally, the temperature accuracy achieved by running the refrigerant cooling subsystem 42 may be higher than that of running just the liquid nitrogen cooling subsystem 40 (where the temperature may tend to bounce sharply above and below the target low temperature). Nevertheless, if the control subsystem 30 determines that the refrigerant cooling subsystem 42 is struggling to maintain the low operating temperature during the steady low temperature phase, the control subsystem 30 is still capable of re-activating the liquid nitrogen cooling subsystem 40 for short periods of time to augment the cooling provided by the refrigerant cooling subsystem 42.

Other temperature control operations are capable of being performed by the environmental control system 10 as well. Such operations include quick heating ramps, maintained heating periods, and so on. Further details will now be provided with reference to FIG. 5.

Figure 5:
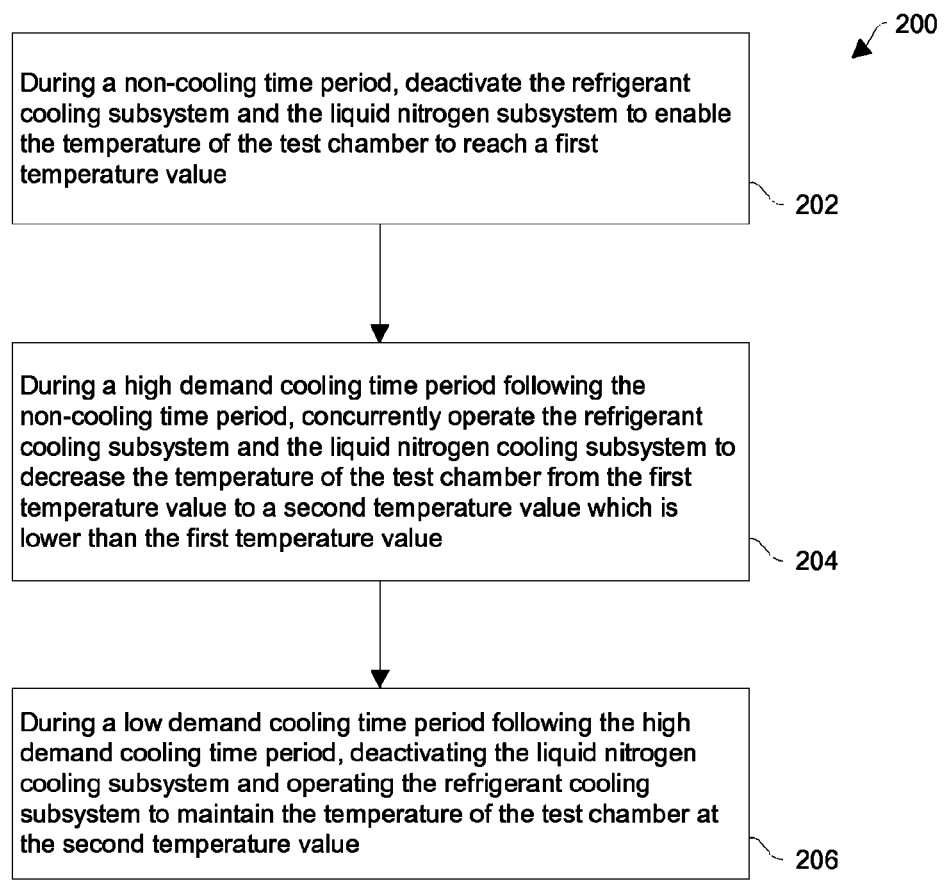
FIG. 5 is a flowchart of a procedure which is capable of being performed by the environmental control system.

FIG. 5 is a flowchart of a procedure 200 which is performed by the environmental control system 10 to control temperature of a test chamber which is equipped with a refrigerant cooling subsystem and a liquid nitrogen cooling subsystem. At 202, during a non-cooling time period such as a hot temperature ramp, the control subsystem of the environmental control system deactivates the refrigerant cooling subsystem and the liquid nitrogen cooling subsystem to enable the temperature of the test chamber to reach a first temperature value.

At 204, during a high demand cooling time period following the non-cooling time period, the control subsystem concurrently operates the refrigerant cooling subsystem and the liquid nitrogen cooling subsystem to decrease the temperature of the test chamber from the first temperature value to a second temperature value that is lower than the first temperature value (e.g., −10 degrees Celsius, −20 degrees Celsius, etc.). Here, both cooling subsystems run in order to provide relatively high cooling capacity to the test chamber.

At 206, during a low demand cooling time period following the high demand cooling time period, the control subsystem deactivates the liquid nitrogen cooling subsystem and operating the refrigerant cooling subsystem to maintain the temperature of the test chamber at the second temperature value. Here, only the refrigerant cooling subsystem runs in order to provide efficient, lower-cost cooling to the test chamber.

It should be understood that one or more additional phases can be inserted before, between, and/or after the above-described steps of the procedure 200 to provide various phases of a test on particular equipment. Along these lines, FIG. 4 shows a series of phases that could be applied in a single test.

As described above, improved techniques are directed to an environmental control system 10 is equipped with a test chamber 20 and a hybrid cooling subsystem 22 to effectuate reliable and robust test chamber cooling. The hybrid cooling subsystem 22 includes (i) a liquid nitrogen cooling subsystem 40 and (ii) a refrigerant cooling subsystem 42. Such a system 10 has the ability to provide effective high demand cooling of the test chamber 20 by concurrently operating the liquid nitrogen cooling subsystem 40 and the refrigerant cooling subsystem 42 (e.g., during a temperature ramp phase 108 in which the temperature of the test chamber is lowered very quickly). Such a system 10 also has the ability to provide efficient low demand cooling of the test chamber 20 by deactivating the liquid nitrogen cooling subsystem 40 and operating just the refrigerant cooling subsystem 42 (e.g., during a temperature soak phase in which the test chamber is maintained at a low temperature). Such selective operation can provide significant cost savings by alleviating the need to provide liquid nitrogen cooling in all cooling situations.

While various embodiments of the present disclosure have been particularly shown and described, it will be understood by those skilled in the art that various changes in form and details may be made therein without departing from the spirit and scope of the present disclosure as defined by the appended claims.

For example, it should be understood that the above-mentioned temperatures were provided for illustration purposes only. Other temperatures are suitable for use as well. Along these lines, the environmental control system 10 is capable of providing test chamber temperatures within a wide range (e.g., above 90 degrees Celsius, below −35 degrees Celsius, any temperatures in between, and so on).

Additionally, it should be understood that it is possible to run different combinations of subsystems to provide different effects. Along these lines, nothing precludes running only the liquid nitrogen cooling subsystem 40 and deactivating the refrigerant cooling subsystem 42 (e.g., if the refrigerant cooling subsystem 42 is not working properly and requires service).

Furthermore, if it determined that the refrigerant cooling subsystem 42 is sufficient for handling all cooling needs, the liquid nitrogen cooling subsystem 40 can be deactivated for an entire test to minimize operating costs. Nevertheless, the liquid nitrogen cooling subsystem 40 for particular applications, test, and operations as desired. Such modifications and enhancements are intended to belong to various embodiments of the disclosure.

Additionally, it should be understood that although some apparatus may not have a feature of being able to pull air from the outside, other apparatus may have such a feature. For example, the air circulation subsystem 26 can generate an airstream at various speeds through a set of baffles which are thermally coupled to coils of the hybrid cooling subsystem 22 and to the heating subsystem 24. For some tests, the air circulation subsystem 26 is substantially closed thus circulating the air internally (e.g., during low or high temperature soaks, during low or high temperature ramps, etc.). For other tests, the air circulation subsystem 26 may utilize ambient external air (e.g., tests at room temperature).

Furthermore, it should be understood that the coil configuration of FIG. 3 enables multiple coil portions to be stacked upon each other in the Z-direction. For example, a coil portion 82 of the refrigerant cooling subsystem 42 can be layered adjacent heating elements of heating subsystem 24 in a co-located formation thus enabling a single airstream to pass through both for augmented air cooling (e.g., laminar air flow across baffles of both portions).

Based on the discussion above, it should be understood that environmental test chambers may be used in Environmental Stress Screening (ESS) test processes to identify early life failures on its products. With the environmental control system 10, both the chamber operations and the test processes that surround legacy ESS processes can be altered. In particular, many conventional test chambers leverage liquid nitrogen (LN2) as its cooling source to maintain temperature set-points (soaks) and also for very fast changes known as temperature ramps. The refrigerant cooling subsystem can operate as a supplementary cooling source (a low cost mechanical cooling source) within the test chamber for temperature soak periods along with the use of LN2 for temperature ramps without negatively impacting the chamber capacity, performance and floor space that the chamber occupies.

For example, a legacy test chamber can be retrofitted with a 5 Hp compressor unit which is located directly or generally on top of the chamber. The unit can be physically secured to the chamber and connected to water infrastructure. The inside of the chamber in the plenum area where the air circulator blowers, liquid nitrogen nozzles and heating coils exist today can be modified to allow a set of cooling coils to fit into this space for a refrigerant cooling subsystem. Such coils can be piped and lagged to a compressor unit on the roof and/or locally above the test chamber. The power and controls of this compressor unit can be integrated to the current chamber controls thus allowing the entire system to operate in sync as a hybrid unit.

As a result, the compressor unit can now become a primary cooling source and only when high demand cooling is required will LN2 be allowed enter the chamber. The ESS chamber can be loaded with devices for ESS testing/screening. As soon as the devices under test are powered on the chamber will always require cooling (e.g., a chamber is a closed space and the product is constantly generating heat). This cooling requirement is low demand cooling. The new compressor unit fitted to the chamber has now enough cooling capacity to counteract the heat from the product under test thus eliminating the requirement for LN2.

All products within their test cycle process can undergo rapid temperature changes to detect defects. Now the compressor unit may need to allow the LN2 into the chamber to achieve rapid cooling and thus achieve the required ramp rate in temperature. This is obtained through a process of using timers perhaps in conjunction with chamber controller PID settings. That is, this process can be developed and tested for various products under test. Once the new temperature set-point has been achieved the LN2 backs out and the compressor unit takes over as the primary cooling source.

It should be understood that conventional ESS Chambers only use LN2 for cooling. LN2 is a very expensive commodity and these chambers are very inefficient at providing low demand cooling. Mechanical only cooled chambers also exist on the market today but are generally twice the size which negatively impacts floor space within a manufacturing site and are significantly more expensive to purchase. They also require a far higher spec infrastructure to support the larger compressors which would require significant capital investment.

However, by introducing a supplementary cooling source, the test chamber is far more economical than previous, delivering significant dollar and sustainability savings. A proof of concept (POC) in certain plants yielded an 85% reduction in the volumes of LN2 consumed across all products within the ESS process. Such a reduction in LN2 use may provide significant savings.

What is claimed is:

1. An environmental control apparatus, comprising:
a test chamber;
a refrigerant cooling subsystem coupled to the test chamber;
a liquid nitrogen cooling subsystem coupled to the test chamber; and
control circuitry coupled to the refrigerant cooling subsystem and the liquid nitrogen cooling subsystem, the control circuitry being constructed and arranged to coordinate operation of the refrigerant cooling subsystem and the liquid nitrogen cooling subsystem to control internal temperature of the test chamber;
wherein the refrigerant cooling subsystem includes a set of refrigerant cooling coils to provide cooling from the refrigerant cooling subsystem;
wherein the liquid nitrogen cooling subsystem includes a set of liquid nitrogen nozzles to provide cooling from the liquid nitrogen cooling subsystem;
wherein the set of refrigerant cooling coils of the refrigerant cooling subsystem provides cooling directly to a set of computerized circuit board devices residing in a center cavity of the test chamber and the set of liquid nitrogen nozzles of the liquid nitrogen cooling subsystem provides cooling directly to the set of computerized circuit board devices residing in the center cavity of the test chamber when the set of computerized circuit board devices continue to reside in the center cavity of the test chamber during a particular electronic test of the set of computerized circuit board devices; and
wherein the environmental control apparatus further comprises:
a common blower which blows air from both the set of refrigerant cooling coils of the refrigerant cooling subsystem and the set of liquid nitrogen nozzles of the liquid nitrogen cooling subsystem in a direction toward the set of computerized circuit board devices residing in the center cavity of the test chamber when the set of computerized circuit board devices continue to reside in the center cavity of the test chamber during the particular electronic test of the set of computerized circuit board devices, and
a vibration assembly coupled to the test chamber, the vibration assembly purposefully imparting physical motion on to the set of computerized circuit board devices residing in the center cavity of the test chamber when the set of computerized circuit board devices continue to reside in the center cavity of the test chamber during the particular electronic test of the set of computerized circuit board devices.

2. An environmental control apparatus as in claim 1 wherein the control circuitry, when coordinating operation of the refrigerant cooling subsystem and the liquid nitrogen cooling subsystem, is constructed and arranged to:
  individually operate each of the refrigerant cooling subsystem and the liquid nitrogen cooling subsystem.

3. An environmental control apparatus as in claim 2 wherein the control circuitry, when individually operating each of the refrigerant cooling subsystem and the liquid nitrogen cooling subsystem, is constructed and arranged to:
  concurrently activate the refrigerant cooling subsystem and the liquid nitrogen cooling subsystem to expose electronic equipment residing in the test chamber to a temperature stress phase in which an internal environment of the test chamber is quickly ramped from an initial temperature to a target temperature which is lower than the initial temperature to stress the electronic equipment while the electronic equipment is operating.

4. An environmental control apparatus as in claim 2 wherein the control circuitry, when individually operating each of the refrigerant cooling subsystem and the liquid nitrogen cooling subsystem, is constructed and arranged to:
  activate the refrigerant cooling subsystem and concurrently deactivate the liquid nitrogen cooling subsystem to expose electronic equipment residing in the test chamber to a constant temperature phase in which an internal environment of the test chamber is maintained at a constant temperature after the internal environment is ramped from an initial temperature to the constant temperature while the electronic equipment is operating.

5. An environmental control apparatus as in claim 2 wherein the control circuitry, when individually operating each of the refrigerant cooling subsystem and the liquid nitrogen cooling subsystem, is constructed and arranged to:
  during a non-cooling phase, deactivate the refrigerant cooling subsystem and the liquid nitrogen cooling subsystem to enable a temperature of the test chamber to reach a first temperature value,
  during a high demand cooling phase following the non-cooling phase, concurrently operate the refrigerant cooling subsystem and the liquid nitrogen cooling subsystem to decrease the temperature of the test chamber from the first temperature value to a second temperature value that is lower than the first temperature value, and
  during a low demand cooling phase following the high demand cooling phase, deactivate the liquid nitrogen cooling subsystem and operate the refrigerant cooling subsystem to maintain the temperature of the test chamber at the second temperature value.

6. An environmental control apparatus as in claim 5 wherein the vibration assembly imparts physical motion to electronic equipment residing in the test chamber while the electronic equipment operates during activation and deactivation of each of the refrigerant cooling subsystem and the liquid nitrogen cooling subsystem.

7. An environmental control apparatus as in claim 5 wherein the control circuitry includes:
  a common control interface to receive user input from a user, and provide user output to the user, the user input including commands to operate the refrigerant cooling subsystem and the liquid nitrogen cooling subsystem, and the user output providing operating status from the refrigerant cooling subsystem and the liquid nitrogen cooling subsystem.

8. An environmental control apparatus as in claim 5 wherein the control circuitry includes:
  a timer to control duration of the non-cooling phase, the high demand cooling phase, and the low demand cooling phase.

9. An environmental control apparatus as in claim 5 wherein the control circuitry includes:
  a proportional-integral-derivative (PID) controller to provide temperature control precision during different cooling phases.

10. An environmental control apparatus as in claim 1, further comprising:
  an air circulation subsystem to generate an air stream within the test chamber, wherein the set of refrigerant cooling coils and the set of liquid nitrogen nozzles are co-located relative to the air circulation subsystem to enable shared access to the air stream.

11. An environmental control apparatus as in claim 10, further comprising:
  a heating subsystem coupled to the control circuitry, a portion of the heating subsystem being co-located with the set of refrigerant cooling coils and the set of liquid nitrogen nozzles to share access to the air stream; and
  wherein the control circuitry is further constructed and arranged to coordinate operation of the heating subsystem with operation of the refrigerant cooling subsystem and the liquid nitrogen cooling subsystem.

12. An environmental control apparatus as in claim 10 wherein the set of refrigerant cooling coils and the set of liquid nitrogen nozzles are co-located adjacent a top region of the test chamber.

13. An environmental control apparatus as in claim 10 wherein the test chamber is constructed and arranged to house, as further electronic equipment, a set of computerized components while the computerized components electronically operate and endure stress testing to identify early life failures.

* * * * *